(12) United States Patent  
Russell et al.

(10) Patent No.: US 8,710,289 B2
(45) Date of Patent: Apr. 29, 2014

(54) WOUND DRESSINGS

(75) Inventors: Malcolm Russell, Herefordshire (GB); Philip Andrews, Wiltshire (GB); Hugh Semple Munro, Wiltshire (GB); Robert Halstead, Wiltshire (GB); David Preece, Herefordshire (GB)

(73) Assignees: First Water Limited, Wiltshire (GB); Prometheus Medical Ltd, Herefordshire (GB)

( * ) Notice: Subject to any disclaimer, the term of this patent is extended or adjusted under 35 U.S.C. 154(b) by 166 days.

(21) Appl. No.: 13/219,385

(22) Filed: Aug. 26, 2011

(65) Prior Publication Data

US 2012/0078153 A1 Mar. 29, 2012

Related U.S. Application Data

(60) Provisional application No. 61/377,373, filed on Aug. 26, 2010.

(51) Int. Cl.
*A61F 13/00* (2006.01)

(52) U.S. Cl.
USPC .................. 602/41; 602/42; 602/43

(58) Field of Classification Search
USPC ....................................... 602/41–54
See application file for complete search history.

(56) References Cited

U.S. PATENT DOCUMENTS

| | | | | |
|---|---|---|---|---|
| 4,615,674 A | * | 10/1986 | Rathmell | 431/215 |
| 4,909,244 A | * | 3/1990 | Quarfoot et al. | 602/48 |
| 5,160,322 A | | 11/1992 | Scheremet et al. | 604/122 |
| 5,195,977 A | | 3/1993 | Pollitt | 604/122 |
| 5,431,633 A | * | 7/1995 | Fury | 604/122 |
| 5,478,333 A | | 12/1995 | Asherman, Jr. | 604/304 |
| 5,662,598 A | * | 9/1997 | Tobin | 602/41 |
| 6,700,031 B1 | * | 3/2004 | Hahn | 602/41 |
| 7,429,687 B2 | | 9/2008 | Kauth et al. | 602/58 |
| 7,495,055 B2 | * | 2/2009 | Soerens et al. | 524/588 |

(Continued)

FOREIGN PATENT DOCUMENTS

| WO | WO 97/24149 | 7/1997 | A61L 15/58 |
|---|---|---|---|
| WO | WO 97/34947 | 9/1997 | C08K 5/00 |

(Continued)

OTHER PUBLICATIONS

Arnaud F. et al., (2008) "Evaluation of chest seal performance in a swine model: comparison of Asherman vs. Bolin seal." Injury, Int. J. Care Injured, Sep; 39(9):1082-1088.

(Continued)

*Primary Examiner* — Michael A. Brown
(74) *Attorney, Agent, or Firm* — Harness, Dickey & Pierce, P.L.C.

(57) ABSTRACT

A dressing for covering a wound of a patient comprises a sheet member adapted to be adhered to the patient's skin in use to provide an airtight seal around the wound, wherein the skin-adhesion is provided by a hydrogel layer 10 on the skin-facing face of the sheet member, wherein the sheet member defines in use a substantially enclosed space 5 above the wound, and wherein a plurality of mutually spaced-apart flutter valves formed by holes 5 in a thin film 13 overlying an upper face of a layer 12 of the sheet member permit one-way air, blood and/or other fluid flow communication from the space 5 above the wound to the exterior of the dressing.

15 Claims, 4 Drawing Sheets

(56) References Cited

U.S. PATENT DOCUMENTS

| | | | |
|---|---|---|---|
| 7,615,674 B2 | 11/2009 | Asherman | 602/58 |
| 7,834,231 B2 * | 11/2010 | Biddle et al. | 602/41 |
| 7,846,141 B2 * | 12/2010 | Weston | 604/313 |
| 2008/0234726 A1 | 9/2008 | Biddle et al. | 606/213 |

FOREIGN PATENT DOCUMENTS

| | | | |
|---|---|---|---|
| WO | WO 00/06214 | 2/2000 | A61L 24/06 |
| WO | WO 00/06215 | 2/2000 | A61L 24/06 |
| WO | WO 00/07638 | 2/2000 | A61L 15/58 |
| WO | WO 00/46319 | 8/2000 | C09J 201/02 |
| WO | WO 00/65143 | 11/2000 | D06N 3/00 |
| WO | WO 01/96422 | 12/2001 | C08F 20/58 |
| WO | WO 2005/039465 | 5/2005 | A61F 13/02 |
| WO | WO 2007/007155 | 1/2007 | B65B 37/12 |

OTHER PUBLICATIONS

Hydrogels, Kirk-Othmer Encyclopedia of Chemical Technology, 4th Edition, vol. 7, pp. 783-807, John Wiley and Sons, New York.

* cited by examiner

WOUND DRESSINGS

CROSS-REFERENCE TO RELATED APPLICATIONS

This application claims the benefit of U.S. Provisional Application No. 61/377,373, filed on Aug. 26, 2010, the entire disclosure of which is incorporated herein by reference.

FIELD

The present invention relates to wound dressings, particularly for use when an essentially one way passage of air and/or fluid are required, as for example in the case of penetrating wounds such as penetrating thoracic trauma. The invention also relates to processes for the manufacture of the compositions, and to uses of these dressings, as well as to a spacer device for use with the dressings.

BACKGROUND

This section provides background information related to the present disclosure which is not necessarily prior art.

The human or animal body has two lungs, each enclosed in a separate airtight area (pleural cavity) within the chest. If an object, for example bullet, shrapnel, knife, blast debris and/or stick penetrates the chest wall an open chest wound results, and allows air to enter one or both of the chest cavity area and the pleural cavity when the person next attempts to inhale. The lung will begin to collapse as a result of the loss of a pressure differential between the chest cavity area or pleural cavity and the air in the trachea, which is at outside pressure.

Any degree of collapse of either lung interferes with the casualty's ability to breath and reduces the amount of oxygen available for use by the body.

It is therefore important, in cases of actual or suspected penetrating thoracic trauma, to apply a dressing that prevents the ingress of air, through the wound in the chest wall, into the chest cavity area or pleural space.

However, if the lung has also been punctured, then air may also enter the pleural space via that route and if not allowed to escape may result in an increase in pressure again resulting in a serious impairment (life threatening) to breathing. The latter case is known as a tension pneumothorax.

Fluids, for example blood, resulting from the trauma may also leak into the pleural space and need to be able to escape.

Consequently any dressing applied to an actual or suspected penetrating chest wound needs to allow the egress of air and fluid from the pleural space but also prevent the ingress of air and fluid.

A number of dressing constructions have been proposed to address this issue.

In U.S. Pat. No. 5,195,977 (assigned to Lohman GmbH & Co), the disclosure of which is incorporated herein by reference, a wound dressing (plaster) is described which has a gas check valve which responds to slight pressure variations. The gas check valve is inserted in an aperture in the plaster. The skin facing side of the plaster is coated with a pressure sensitive adhesive. The gas check valve may be of a diaphragm, ball, plug or spring type. No exemplification of the slight pressure variation required to activate the valve is given. The pressure sensitive adhesive used is described as a rubber adhesive or an acrylic adhesive.

U.S. Pat. No. 5,160,322 (assigned to Brunswick Biomedical Technologies Inc.), the disclosure of which is incorporated herein by reference, describes a one-way valve which permits the outward flow of air and liquid from the chest cavity but closes against the same flow of atmospheric air into the chest cavity. A dome protruding from the outward facing surface of the dressing protects the valve element.

U.S. Pat. No. 7,615,674 (Asherman), the disclosure of which is incorporated herein by reference, describes a dressing comprising a one way valve which is rigid to prevent obstruction of the valve arising from turning of the patient's clothing.

U.S. Pat. No. 7,429,687 (assigned to The Seaberg Company Inc.), the disclosure of which is incorporated herein by reference, describes an adhesively attachable bandage comprising a valve assembly with a rigid cover. The adhesive is preferably an aggressive hydrogel or hydrocolloid possessing good wet tack and so are able to adhere to damp skin. However, no description is provided for specific examples of suitable materials.

U.S. Pat. No. 5,478,333 (Asherman), the disclosure of which is incorporated herein by reference, describes a dressing comprising a flexible body with adhesive on one side for attaching the body to the skin of the patient. The centre of the body is formed into a flexible tubular duct which projects away from the patient. A flexible one way valve is mounted to the exterior of the duct to allow the passage of air fluid out of the wound but preventing air being drawn back into the wound through the duct.

U.S. Pat. Application 2008/0234726 A1, the disclosure of which is incorporated herein by reference, describes a chest seal dressing with a low profile one way valve also comprising a biocompatible adhesive. Suitable adhesives for adhering the flange body to the patient's skin include hydro gel, acrylic, silicone gel, silicone PSA or hydrocolloid. No specific examples are disclosed. The passage of fluid is not described.

Due to the complexity of the valve arrangements disclosed in the prior art the cost of these dressings is high. In addition, the valve constructions in all of the above prior art systems have a substantially greater thickness than the skin-adhesive portions of the dressing in the major face to major face direction of the dressing, and have hard or rigid portions which can press into the wound if the patient's weight or some external force presses on the dressing. Some of the valves (e.g., the valve of U.S. Pat. No. 5,478,333 to Asherman) can become closed permanently simply by the patient lying awkwardly.

WO-A-2005/039465, the disclosure of which is incorporated herein by reference, describes an attempt to solve at least some of the above problems. The dressing described has a bandage section which overlies the wound and is sealed to the skin around a perimeter to enclose a space above the wound, and a single flutter valve mouth which provides one-way fluid flow communication between the space above the wound and the exterior environment. The valve lies substantially in the same plane as the bandage section. Nevertheless, the valve of this prior art is still bulky in that at least four sheets of material (FIG. 6) are required for its construction, and a rigid outer casing is specified as most preferred (page 4, lines 19 to 23; page 11, lines 9 to 16). Embodiments in which an additional fluid inlet valve is provided for flushing-out the flutter valve are described, which is no longer planar with the remainder of the device (FIGS. 8 to 10).

There is general concern that chest seals used for treatment of open chest wounds can fail due to coagulation or malfunction of the external vent and poor skin adherence. Chest seal failure may lead to respiratory compromise or the development of a tension pneumothorax. (Arnaud F. et al., Evaluation of chest seal performance in a swine model: comparison of Asherman vs. Bolin seal. Injury, 2008 September; 39(9): 1082-8.). The disclosure of this publication is incorporated herein by reference.

Dressings adapted to permit essentially one way fluid flow away from a wound may also find use in special circumstances, such as where a managed flow of blood from a wound, or a managed restriction or prevention of contact between external sea water and the wound is required.

The present invention as described below provides an alternative, and improved dressing, over those disclosed in the prior art. The present invention may overcome or mitigate at least one or more problems associated with the dressings of the prior art.

SUMMARY

In a first aspect of the present invention, there is provided a dressing for covering a wound of a patient, for example in the case of a penetrating chest wound to assist the patient's breathing, comprising a sheet member adapted to be adhered to the patient's skin in use to provide an airtight seal around the wound, the sheet member being adapted to be spaced apart from the skin in the region of the wound to define in use a space above the wound, and a plurality of mutually spaced-apart flutter valves being provided permitting one-way air, blood and/or other fluid flow communication from the space above the wound to the exterior of the dressing.

In a second aspect of the present invention, there is provided a method of manufacturing a wound dressing according to the first aspect of the present invention, comprising assembling the parts thereof in juxtaposition suitable for forming the dressing and securing the same together to provide the dressing.

At least one, preferably all, of the flutter valves may comprise one leaflet, that is: one moveable leaf which can be moved away from a relatively fixed base surface by the flow of air and/or liquid out of the valve, to open the valve in a one-way manner. However, if desired a two leaflet flutter valve construction may be employed in at least one of the valves.

The sheet member of the dressing is suitably flexible and skin-conformable. The whole dressing, including the flutter valves, is suitably formed solely from sheet materials which are of sufficient flexibility that the whole dressing is skin-conformable and has no hard or rigid parts.

It is preferred that the sheet member is a multilayer sheet member having a first layer nearest the patient's skin in use and at least one additional layer overlying at least a portion of the first layer on the major face thereof directed away from the patient's skin in use.

The first layer is preferably provided with a skin-adhesive coating on the major face that is directed towards the patient's skin in use, and an aperture is preferably provided in the said first layer, preferably at the centre of the dressing, so that the first layer can surround the wound, but not adhere to it, when the first layer is positioned on the patient's skin to surround the wound and adheres to the patient's skin around the wound to provide a completely airtight seal to the skin around the wound.

For improved airtight sealing around the wound, a second layer, formed of a sheet material that is more flexible and optionally thinner than the material of the first layer, may be laminated to the first layer over that portion of the major face of the first layer that is directed away from the patient's skin in use that surrounds the aperture, the second layer being provided with a smaller aperture than the aperture of the first layer. When the second layer is laminated to the first layer over the aperture-surrounding portion of the first layer, a flange defined by the second layer extends beyond the periphery of the aperture and into the aperture. By providing the major face of the flange that is directed towards the patient's skin in use with a skin-adhesive coating, the flange can provide an additional airtight seal to the patient's skin around the periphery of the aperture, restricting contact between wound fluids and the skin-adhesive coating on the skin-directed major face of the first layer.

At least one, preferably each, of the plurality of flutter valves may be formed by means comprising a further film layer, preferably more flexible and thinner than the other layer or layers of the dressing, which overlies the wound encircling aperture above the major face of the sheet member that is directed away from the skin in use, and extends radially outwardly thereof to overlie a portion of the sheet member around the aperture. The further film layer is non-adhesive both in its region that overlies over the aperture and the region that extends radially outwardly thereof. The further film layer is sealed airtightly to the sheet, radially inward from the outermost border of the sheet member, around most of the periphery of the further film layer, with a plurality of small peripheral portions (holes) being left unsealed, said holes defining the mouths of the plurality of flutter valves of the dressing.

In this way, the dressing is very efficiently constructed so as to provide an essentially planar structure without hard or rigid valve members.

By providing a plurality of flutter valves, the need to orientate the dressing to deliberately position a valve in a gravitationally downward direction is eliminated or reduced. It is preferred to have at least three, for example three, four, five or six, valve mouths, to maximise the advantage of gravitational draining of liquids from the dressing. The plurality of flutter valves are provided in mutually spaced-apart relationship. A wide range of spacing arrangements of the flutter valves is possible. It is preferred that the flutter valves are spaced generally evenly around the periphery of the part of the dressing defining the space above the wound. Thus, for example, in a rectangular (including square) dressing, four flutter valves may be provided, one on each half-diagonal of the dressing. In a circular dressing, two, three, four or five, for example, flutter valves may be provided, spaced angularly evenly around the dressing. The maximum number and the closest spacing of the flutter valves depends on the size of the dressing, the task it is intended to perform, and the required size of the mouth of each flutter valve.

The flutter valves provide the only route for air and/or liquids to leave the space defined by the dressing over the wound. Therefore, the space above the wound defined by the dressing is said to be substantially enclosed when the dressing is in position in use.

The dressing of the present invention therefore enables a dressing having a low profile multiple apertured flutter valve allowing for the one-way outward passage of air and fluid away from the wound and being activated by a low pressure differential.

The dressing may comprise one or more additional layers if desired. Where layers are to be sealed together over an area of their major faces they may suitably be laminated together via an adhesive interfacing layer, via heat sealing (welding), by ultrasound sealing (welding), by gluing or in any other conventional way. Where layers are to be sealed together over a smaller region, for example along a line, they may suitably be sealed together via an adhesive interfacing line, via linear heat sealing (welding) or in any other conventional way.

An example of an additional layer that may be provided is a further layer, e.g., of a woven or non-woven fabric, that may be provided on the major face of the first layer that is directed away from the patient's skin in use, to render the outward face of the dressing non-adhesive. This said further layer may suitably cover the first layer only over its part that lies radially outwardly of the flutter valves around the wound. Preferably the outer periphery of this further layer is coterminous with that of the first layer (length and width)

Further, the adhesives used to laminate or seal parts of the dressing together may be considered as layers.

Further, the skin-adhesive coating provided on the sheet member or parts thereof may be considered as a layer.

A further example of an additional layer is a spacer device that may be provided on the major face of the first layer that is directed away from the patient's skin in use, to provide one or more outwardly extending projection in the region of one or more of the flutter valves, serving to space external objects such as clothing, blankets, and thermal insulating sheets away from the dressing to prevent the flutter valves from being pressed closed by the external objects. A feature of the spacer device is that it must maintain a fluid flow path between one or more of the flutter valves and the external atmosphere. Therefore, if the outwardly extending projection completely encircles an air space above the flutter valves, or in other ways might impede air flow between one or more of the flutter valves and the external atmosphere, the projection is provided with through holes which allow air to pass from the encircled region above the flutter valves to the external atmosphere even if an external object such as clothing, a blanket or a thermal insulating sheet is laid over the dressing.

In accordance with a further aspect of the present invention, there is provided a spacer device for use with a dressing according to the present invention, the spacer device being adapted to be stuck to the face of the dressing that is directed away from the patient's skin in use, wherein the device comprises one or more outwardly extending projection which in use extend in the region of one or more of the flutter valves of the dressing and serve to space external objects such as clothing, blankets, and thermal insulating sheets away from the dressing to prevent the flutter valves from being pressed closed by the external objects, apertures being present through the projection(s) and/or between projections so that air, blood or other fluids can pass from a space above the flutter valves to the external atmosphere when the spacer is in place on the dressing, if an external object such as clothing, a blanket or a thermal insulating sheet is laid over the dressing and spacer.

A release sheet of conventional construction may also be provided to protect the ski-adhesive parts of the dressing or the spacer device before use.

The dressing is preferably sterile-packed in a sealed flexible pack prior to use, in conventional manner.

The skin-adhesive coating used in the dressing of the present invention may comprise any suitable skin-compatible adhesive that permits an airtight seal around the wound and prevents the dressing from becoming dislodged in normal use over a normal residence time on the skin.

The skin-adhesive coating may suitably comprise one or more gels (including hydrogels), hydrocolloids, pressure-sensitive adhesives or any combination thereof. Hydrogels are preferred on account of their non-aggressive adhesion to skin which enables the dressing to be removed without pulling the skin or hair unduly. In addition, hydrogels can be formed into flexible self-supporting sheets and can be engineered to have special desirable properties. Such properties include, for example, ability to adhere well to wet or greasy skin, and water-unstability, by which is meant that contact with water can actually increase the adhesion to the skin, rather than decrease it as is typically found with conventional adhesives. Examples of suitable hydrogel skin adhesives are described below.

The material and thickness of the sheet member is suitably selected to provide backing support to the skin-adhesive coating of the dressing, depending on the inherent mechanical strength of the skin-adhesive.

Optionally one or more of the parts of the dressing may be made in transparent or translucent material. For example, it may assist the carers of a patient suffering from a serious trauma injury to be able to visualise the flows of air and/or fluids into and out of the space above the wound enclosed by the dressing. The portion of the dressing that covers that space may, for example, be made from a transparent or translucent material for that reason.

The dressing may be adapted for human or animal use.

The dressing of the present invention may be connected to one or more fluid collection bag, to collect fluid that may emerge via the flutter valves. In one embodiment, a fluid collection bag for use with the present invention may comprise a flexible receptacle having a mouth and a flange disposed around the mouth, the flange being coated with an adhesive so the flange may adhere to the outwardly directed surface of the dressing of the present invention in use, encircling at least one of the flutter valve mouths, preferably at least the gravitationally lowest one or more or the flutter valve mouths, and most preferably not all of the flutter valve mouths simultaneously. The assembly of the dressing and the collection bag thereby provides a system which contains all or most of the liquids expelled from the wound, while still permitting the one-way airflow communication from the space above the wound to the exterior of the dressing.

We have found that the chest seal dressings have a surprisingly low threshold valve-opening overpressure, by which is meant the air overpressure between the skin-directed major face of the dressing and the opposite major face of the dressing (the air at said opposite major face is normally at atmospheric pressure) at which the one-way valve system of the dressing opens to permit air and other fluid to flow out through the dressing. Moreover, the low threshold valve-opening overpressure of the chest seal dressings is remarkably constant and well-maintained across different samples of dressings according to the present invention, different test or operation procedures, different storage ages of dressings and different lengths of use of dressings. Moreover, these advantages are maintained over a wide range of embodiments of materials and construction details, typical details of which are given herein.

For example, we have found that the chest seal dressings according to the present invention consistently have a threshold valve-opening overpressure of less than about 2.2 cm $H_2O$, more preferably less than about 1.5 cm $H_2O$, and more preferably less than about 1 cm $H_2O$, as measured using the test method described in Example 2 below.

Chest seal dressings having such a low threshold valve-opening overpressure are not available in the prior art.

Therefore, according to a further aspect of the present invention, there is provided a dressing for covering a wound of a patient, for example in the case of a penetrating chest wound to assist the patient's breathing, comprising a sheet member adapted to be adhered to the patient's skin in use to provide an airtight seal around the wound, and one or more valve being provided permitting one-way air, blood and/or other fluid flow communication from a space above the wound to the exterior of the dressing, wherein the dressing has a threshold valve-opening overpressure of less than about 2.2 cm H$_2$O, for example as measured using the test method described in Example 2 below.

The dressing defined in the preceding paragraph preferably has a threshold valve-opening overpressure of less about 1.5 cm H$_2$O, and more preferably less than about 1 cm H$_2$O.

The dressing is preferably a chest seal dressing, more preferably a dressing as described according to any one or more of the other aspects or embodiments of the present invention.

The low threshold valve-opening overpressure of the dressing described and claimed herein is preferably constant within the defined low range across a range of individual dressings manufactured in the same or different batches, for example across at least 100 different dressings.

The low threshold valve-opening overpressure of the dressing described and claimed herein is preferably constant within the defined low range across a range of different storage ages of individual dressings, for example across dressings stored for between 5 days and 800 days at room temperature and pressure. In particular, the dressings of the present invention maintain their performance even when stored in a distorted condition or under pressure from other articles. This contrasts with the prior art dressings that incorporate valves, where distortion or pressure can cause the valve parts to distort or self-seal or self-open, so that the valve becomes inoperable for its medical purpose.

DETAILED DESCRIPTION

Constructions of the Dressing

In one embodiment the dressing as provided ready for use may comprise four superimposed layers.

In this embodiment a conventional release sheet constitutes a bottom layer, not counted in the four.

Overlain over the total upper surface of the bottom layer, and provided with an aperture—preferably a central aperture—where the wound will be in use, is a first layer of the dressing itself, constituted by a skin-adhesive layer.

Overlain over the total upper surface of the skin-adhesive layer, and also provided with a corresponding aperture where the wound will be in use, is a layer of a backing material for the dressing (second layer) such as a woven or non-woven fabric, which provides mechanical support to the skin-adhesive layer and prevents the upper surface of the skin-adhesive layer from sticking to external objects in use. The backing material is suitably chosen for strength and lightness, as well as flexibility and skin-conformability, and to provide a pleasant touch sensation when touching the external surface of the dressing directed away from the skin.

Overlain over the upper surface of the backing material layer (but preferably not over the total area of the backing material) is a third layer which provides an anchor for sealing the fourth layer (described below) that forms the moveable parts of the flutter valves. The third layer of the dressing is provided with an aperture generally corresponding to the apertures of the first and second layers where the wound will be in use. Preferably, however, the aperture in the third layer is smaller than the aperture in the first and second layers described previously, so that a flange of the material of the third layer extends into the aperture of the first and second layers around its periphery, for example by a distance of about 0.2 to about 1 cm, preferably about 0.5 cm. By selecting the material of the third layer to be of suitable flexibility, and providing a suitable skin-adhesive coating on the underside of the flange, the flange can in use stick to the skin surrounding the wound and thereby enhance the air-tight seal around the wound as well as restricting direct contact between blood and other wound fluids and the skin-adhesive of the first layer.

The fourth layer is overlain on the upper surface of the third layer (either over the total area of the third layer or a portion thereof), and is formed of a thin film having sufficient flexibility to serve as the moveable portions of the plurality of flutter valves. This layer has no aperture corresponding to the apertures of the first to third layers mentioned above, but instead a plurality of holes near its periphery, these holes being dimensioned and arranged to serve in use as the mouths of the flutter valves. The fourth layer is non-adhesive on both major faces, and is sealed to the upper surface to the third layer in a seal line around its periphery, ensuring that the holes are free to open and close in use in flutter valve manner, cooperating with the underlying portion of the upper surface of the third layer. The holes of the fourth layer are preferably cut or punched in the material of the fourth layer, and shaped to have minimal sharp corners of other points where the material can become stressed during working of the flutter valves. The holes are most preferably generally circular, elliptical or lenticular in shape over at least the portion of their edges that is at risk of highest degrees of stress in use.

The first layer and fourth layer, in use, are typically in fluid communication with the wound. At least part of one surface, optionally all of one surface, of the first layer may be exposed for contacting a wound. Optionally, one or more further apertured layers and/or materials may be disposed between the wound and the first and/or fourth layer such that portions of the first layer still contact the skin. Examples of such additional materials include nets and nets with antimicrobial properties.

The layers are suitably secured together by appropriate conventional means, for example gluing, melt-welding, heat welding, ultrasound welding, or any combination thereof. Of course, where a layer has its own adhesiveness, it may be adhered directly to an adjacent layer.

Treatments

The dressing of the present invention may suitably be used for dressing a penetrating chest wound and particularly for the prevention of tension pneumothorax.

Manufacture

The present invention also provides a method of manufacturing of the dressing according to the first aspect of the invention.

The method, which constitutes a third aspect of the present invention, comprises assembling the parts thereof in juxtaposition suitable for forming the dressing and securing the same together to provide the dressing, for example using conventional securing means.

For example the embodiment of the invention described above may be manufactured by assembling and adhering together the first and second layers, optionally with one or more further layers and/or materials disposed between the layers, to form a multilayer composite, and subsequently cutting or punching out the gap where the wound will be accommodated in use. Then the third and fourth layers, optionally with one or more further layers and/or materials disposed between the layers and/or between the third and second layers, may be assembled and secured in place. The assembling may comprise forming one or more of the first, second and third layers, in situ, such that, once formed, the layer is adhered to one or more of the other layers in the dressing.

Physical Properties of the Dressing

The dressing is preferably flexible, preferably skin conformable. The dressing is preferably adapted to keeping a wound moist Skin-Adhesive The skin-adhesive layer (coating) and optionally any backing layer to support it is/are preferably compressible.

The skin-adhesive material is preferably a self-supporting material.

The skin-adhesive layer, in use, preferably can removably adhere to skin and/or a wound.

The skin-adhesive is preferably a viscoelastic material. Viscoelastic materials are known to the skilled person. A viscoelastic material typically has one or more of the following properties: (i) hysteresis in the material's stress-strain curve; (ii) stress relaxation occurs in the material: step constant strain causes decreasing stress; and (iii) creep occurs in the material: step constant stress causes increasing strain. A viscoelastic material typically loses energy when a load is applied and then removed. The first layer will typically comprise two opposing surfaces, which can be termed first and second surfaces, one of which may be exposed at least in part for contacting a wound.

The skin-adhesive material suitably comprises a gel, preferably a hydrogel. A "gel" includes, but is not limited to, a self-supporting, flexible substance, optionally comprising one or more polymers. A gel may comprise water. The first material is preferably a viscoelastic hydrogel. The first layer may consist essentially of or consist of a gel, for example a hydrogel, and any water contained therein. It may also comprise a scrim (supportive mesh) within the gel "Consist essentially of" in this context includes, but is not limited to, the first layer comprising about 25 wt % or less, preferably about 20 wt % or less, of components other than the gel and any water it may contain.

Other Optional Features, e.g., Other Layers, of the Dressing

The second layer may comprise two opposed major faces, one or both of which may have a pressure sensitive adhesive thereon, for adhesion to one or more of the other layers in the composition, for example the first and third layers. In an embodiment of the invention the second layer is preferably permeable to moisture vapour. In a further embodiment of the invention the second layer is preferably a non-woven fibre-based fabric. The upper surface of the second layer material may, in use, constitute at least part of outermost surface of the dressing.

The third layer provides a backing layer to the first layer to cover the adhesive first layer and to provide a base for the attachment of the flutter valve assembly to the first layer. The third layer will typically comprise two opposed major faces, one of which, in use, will face the wound and the other of which will face away from the wound. The wound-facing face of the third layer may have disposed thereon a pressure sensitive adhesive for adhesion to other layers of the composite, for example the second layer. The pressure sensitive adhesive may form a continuous or discontinuous coating on the skin-facing face of the third layer. Preferably, the face of the third layer facing away from the wound does not have an adhesive thereon. In am embodiment of the invention the third layer may extend beyond the margins of the aperture (gap) in the first and/or second layer to minimize any contact between the adhesive first layer and the outermost layer which provides the moving parts of the flutter valves, namely a seal on inspiration and may open on expiration during the breathing cycles.

An optional fifth layer may be present to bond the third and fourth layers and may comprise a double-sided adhesive. In the absence of the fifth layer the fourth layer may be directly bonded to the third layer by means of an adhesive (complete or partial covering) on the non-wound-facing face of the third layer, or an adhesive may be partially coated around the perimeter of the wound-facing face of the fourth layer. Other means of adhering the third layer to the fourth layer will be evident to those skilled in the art and include but not limited to welding by heat or ultrasonic means.

The fourth layer comprises a film material possessing sufficient strength and flexibility to seal the preferably central located apertures in all the other layers of the dressing during inspiration and to move outwards during expiration if the pressure in the inter pleural cavity is too high. In a preferred embodiment there are more than one apertures in the fourth layer located such that there is no direct overlap with any of the apertures present in the other layers of the dressing. The apertures in the fourth layer are of a sufficiently large dimension to permit a reasonable flow of fluid (if present) away from the body during expiration but not of dimension sufficiently large to prevent the dressing from acting as a seal during inspiration.

Release liner layers may be applied to the exposed upper and lower surface of the multilayer dressing to facilitate ease of handling and packaging, as previously mentioned.

In one embodiment, the first layer may be thicker than the second layer.

In one embodiment, the second layer may be thicker than the third layer.

The first layer may suitably have a thickness of about 0.1 mm or more, more preferably about 0.3 mm or more, more preferably about 0.5 mm or more and even more preferably about 1 mm or more. The aperture (gap) is preferably centrally located with respect to the area of the layer and maybe of any shape including but not limited to a circle, square, diamond, rectangle or oval. The aperture has an area greater than about $20\,mm^2$, preferably greater than about $50\,mm^2$ and preferably greater than about $100\,mm^2$.

The second layer may have a thickness of about 0.1 mm or more, more preferably about 0.2 mm or more, and even more preferably about 0.4 mm or more. The second layer preferably has a thickness of about 2 mm or less, more preferably about 1 mm or less. The aperture (gap) is preferably centrally located with respect to the area of the layer and maybe of any shape including but not limited to a circle, square, diamond, rectangle or oval. Preferably the aperture is of the same shape and dimension and orientation as the aperture in the first layer. The aperture has an area greater than about $20\,mm^2$, preferably greater than about $50\,mm^2$ and preferably greater than about $100\,mm^2$.

The third layer, including any optional adhesive layer which may be disposed on a surface of the third layer, may have a thickness of about 0.03 mm or more, more preferably about 0.07 mm or more and even more preferably about 0.1 mm or more. The aperture (gap) is preferably centrally located with respect to the area of the layer and maybe of any shape including but not limited to a circle, square, diamond, rectangle or oval. The aperture has an area greater than about $20\,mm^2$, preferably greater than about $50\,mm^2$ and preferably greater than about $100\,mm^2$.

In a preferred embodiment the area of the aperture in the third layer is less than the area of the apertures in the first or second layers such that the third layer overlaps the margins of the aperture formed by the first and second layers. The outer perimeter of the third layer is preferably less than that of the first and second layers.

The fourth layer may have a thickness of about 0.01 mm or more, more preferably about 0.015 mm or more, more preferably about 0.02 mm or more and preferably less than about 0.5 mm. Preferably the fourth layer has a more than one aperture. Each aperture is preferably located off centre with respect to the area of the layer and maybe of any shape including but not limited to a circle, square, diamond, rectangle or oval. The area of the individual apertures in the fourth layer is preferably greater than about 10 mm$^2$, more preferably greater than about 15 mm$^2$ and even more preferably greater than about 18 mm$^2$ but preferably less than about 40 mm$^2$. The sizes of the apertures in the fourth layer reflect the internal areas of commonly used chest drain tubes.

The optional fifth layer described above, when present, may have a thickness of about 0.02 mm or more, more preferably about 0.05 mm or more, more preferably about 0.1 mm or more and preferably less than about 0.5 mm. The outer perimeter of the fifth layer is preferably less that that of the first and second layers. The aperture in the fifth layer suitably has an area greater that that of the first or second layers such that the first and second layers extend beyond the margin of the aperture in the fifth layer when the layers are superimposed in the dressing.

Spacer Device

The spacer device is suitably constructed in the form of a complete or partial ring of rigid sheet material having a face-to-face thickness suitably up to about 2 cm, preferably about 0.2 to about 0.5 cm, for example about 0.25 cm, with an adhesive provided on one major face so that the spacer can be stuck to the face of the dressing that is directed away from the patient's skin in use. The size of the ring is suitably such as to encircle all the flutter valves of the dressing. The ring may be any suitable shape, and we have found that a shape corresponding generally to the shape of the dressing, but a little smaller than the outside limits of the dressing, is suitable. The spacer can, for example, have through-holes passing between the radially inward and radially outward sides of the ring, which allow air to pass from the encircled region above the flutter valves to the external atmosphere when the spacer is in place on the dressing, when an external object such as clothing, a blanket or a thermal insulating sheet is laid over the dressing and spacer. For example, the spacer device may be formed of a corrugated plastic sheet material cut or pressed into the desired shape (e.g., a ring) and provided with an adhesive layer on one face.

Gels

The skin-adhesive, e.g., comprising the first layer, preferably comprises a hydrocolloid, a hydrogel or other viscoelastic gel.

The gel may comprise, consist essentially of or consist of a cross-linked hydrophilic polymer of a hydrophilic monomer and optionally one or more comonomers, together with water and/or one or more organic plasticiser, and optionally together with one or more additives selected from surfactants, polymers, pH regulators, electrolytes, chloride sources, bioactive compounds (including antimicrobial agents) and mixtures thereof, with less than about 30% by weight of other additives.

The skin-adhesive may comprise a hydrocolloid. The hydrocolloid may be selected from sodium carboxymethylcellulose, pectin, gelatine, guar gum, locust bean gum, karaya gum, and mixtures thereof.

The skin-adhesive may alternatively comprise a pressure sensitive acrylic adhesive.

Preferably, the skin-adhesive comprises a hydrogel. The expression "hydrogel" and like expressions, used herein, are not to be considered as limited to gels which contain water, but extend generally to all hydrophilic gels, including those containing organic non-polymeric components in the absence of water. The gel forming agent may, for example, be selected from natural hydrophilic polymers, synthetic hydrophilic polymers, hydrocolloids, gelling hydrophilic biopolymers and all combinations thereof.

Hydrogels are, generally speaking, hydrophilic polymers characterized by their hydrophilicity (i.e., capacity to absorb large amounts of fluid such as wound exudate) and insolubility in water: i.e., they are capable of swelling in water while generally preserving their shape.

The hydrophilicity is generally due to groups such as hydroxyl, carboxy, carboxamido, and esters, among others. On contact with water, the hydrogel assumes a swollen hydrated state that results from a balance between the dispersing forces acting on hydrated chains and cohesive forces that do not prevent the penetration of water into the polymer network. The cohesive forces are most often the result of crosslinking, but may result from electrostatic, hydrophobic or dipole-dipole interactions.

Useful classes of hydrogels in the present invention include those polymers and copolymers derived from acrylic and methacrylic acid ester, including hydroxyalkyl (meth)acrylates, 2-(N,N-dimethylamino)ethyl methacylate, methacryloyloxyalkyl sulfonates (generally crosslinked with diacrylate or divinylbenzene), polymers and copolymers of substituted and unsubstituted acrylamides, polymers and copolymers of N-vinylpyrrolidinone, and polyelectrolyte complexes. Hydrogels are described in greater detail in Hydrogels, Kirk-Othmer Encyclopedia of Chemical Technology, 4th Edition, vol. 7, pp. 783-807, John Wiley and Sons, New York, the contents of which are incorporated herein by reference.

The term "hydrogel" is used herein regardless of the state of hydration.

The hydrogel used in connection with the present invention will suitably comprise a substantially water-insoluble, crosslinked, partially neutralized, gel-forming polymer material. Such hydrogel materials can be prepared from polymerisable, unsaturated, acid- and ester-containing monomers. Examples of such monomers are described in more detail below.

The hydrogel used in the present invention preferably comprises a plasticised three-dimensional matrix of cross-linked polymer molecules, and has sufficient structural integrity to be self-supporting even at very high levels of internal water content (e.g., a water content of at least 20%, optionally 50%, by weight) with sufficient flexibility to conform to the surface contours of mammalian skin or other surface with which it is in contact.

The hydrogel generally comprises, in addition to the cross-linked polymeric network, an aqueous or non-aqueous plasticising medium including an organic plasticiser. This plasticising medium is preferably present in the same precursor solution as the monomer(s).

The precursor liquid can comprise a solution of the gel-forming polymer in a relatively volatile solvent, whereby the hydrogel is deposited as a residue on evaporation of the solvent, or—more preferably—the precursor liquid will comprise a solution of the monomer(s), cross-linking agent, plasticiser, and optionally water and other ingredients as desired, whereby the hydrogel is formed by a curing reaction performed on the precursor liquid after application to the substrate to which the hydrogel is to be applied.

In the following discussion, the second form of precursor solution and application protocol (in situ polymerisation of the hydrogel) will be discussed. The solvent deposition method carried out on a pre-formed gel-forming polymer is well known and the details of that procedure do not need to be reproduced here.

The polymerisation reaction is preferably a free-radical polymerisation with cross-linking, which may for example be induced by light, heat, radiation (e.g., ionising radiation), or redox catalysts, as is well known.

For example, the free radical polymerisation may be initiated in known manner by light (photoinitiation), particularly ultraviolet light (UV photoinitiation); heat (thermal initiation); electron beam (e-beam initiation); ionising radiation, particularly gamma radiation (gamma initiation); non-ionising radiation, particularly microwave radiation (microwave initiation); or any combination thereof. The precursor solution may include appropriate substances (initiators), at appropriate levels, e.g., up to about 5% by weight, more particularly between about 0.002% and about 2% by weight, which serve to assist the polymerisation and its initiation, in generally known manner.

Preferred photoinitiators include any of the following either alone or in combination: Type I-hydroxy-ketones and benzilidimethyl-ketals e.g., Irgacure 651. These are believed on irradiation to form benzoyl radicals that initiate polymerisation. Photoinitiators of this type that are preferred are those that do not carry substituents in the para position of the aromatic ring. A particularly preferred photoinitiator is 1-hydroxycyclohexyl phenyl ketone; for example, as marketed under the trade name Irgacure 184 by Ciba Speciality Chemicals. Also preferred are Daracur 1173 (2-hydroxy-2-propyl phenyl ketone) and mixtures of Irgacure 184 and Daracur 1173. Photo-polymerisation is particularly suitable, and may be achieved using light, optionally together with other initiators, such as heat and/or ionizing radiation. Photoinitiation will usually be applied by subjecting the pre-gel reaction mixture containing an appropriate photoinitiation agent to ultraviolet (UV) light. The incident UV intensity, at a wavelength in the range from 240 to 420 nm, is typically greater than about 10 mW/cm$^2$. The processing will generally be carried out in a controlled manner involving a precise predetermined sequence of mixing and thermal treatment or history. The UV irradiation time scale should ideally be less than 60 seconds, and preferably less than 10 seconds to form a gel with better than 95% conversion of the monomers. Those skilled in the art will appreciate that the extent of irradiation will be dependent on a number of factors, including the UV intensity, the type of UV source used, the photoinitiator quantum yield, the amount of monomer(s) present, the nature of the monomer(s) present and the presence of polymerisation inhibitor. In one preferred embodiment, (on the one hand) the precursor solution in contact with the substrate to which it is to be applied and (on the other hand) the source of the polymerisation initiator (e.g., the radiation source) may move relative to one another for the polymerisation step. In this way, a relatively large amount of polymerisable material can be polymerised in one procedure, more than could be handled in a static system. This moving, or continuous, production system is preferred. After completion of the polymerisation, the product is preferably sterilised in conventional manner. The sterile composite may be used immediately, e.g., to provide a skin-adhesive layer in an article, or a top release layer may be applied to the composite for storage and transportation of the composite. If desired, certain ingredients of the hydrogel may be added after the polymerisation and optional cross-linking reaction. However, it is generally preferred that substantially all of the final ingredients of the hydrogel are present in the precursor solution, and that—apart from minor conventional conditioning or, in some cases, subsequent modifications caused by the sterilisation procedure—substantially no chemical modification of the hydrogel takes place after completion of the polymerisation reaction.

Monomers

The gel preferably comprises a polymer having pendant sulphonyl groups, and optionally pendant carboxylic acid groups in acid or salt form. The hydrogel used in the present invention suitably may comprise a substantially water-insoluble, crosslinked, at least partially neutralized, gel-forming polymer material having the pendant sulphonyl groups, and optionally pendant carboxylic groups, in acid or salt form at least at its wound-contacting surface. The hydrogel polymer materials can be prepared from polymerizable, unsaturated, acid- and ester-containing monomers. The hydrogel polymer may be present at the wound-contacting surface of the composition and contain pendant sulphonyl groups, in acid or salt form, and optionally carboxylic groups in acid or salt form. Thus, such monomers include the olefinically unsaturated acids, esters and anhydrides which contain at least one carbon to carbon olefinic double bond. More specifically, these monomers can be selected from olefinically unsaturated carboxylic acids, carboxylic esters, carboxylic acid anhydrides; olefinically unsaturated sulphonic acids; and mixtures thereof.

Olefinically unsaturated carboxylic acid, carboxylic acid ester and carboxylic acid anhydride monomers include the acrylic acids typified by acrylic acid itself, methacrylic acid, ethacrylic acid, α-chloroacrylic acid, α-cyano-acrylic acid, β-methyl-acrylic acid (crotonic acid), α-phenyl acrylic acid, β-acryloxy-propionic acid, sorbic acid, α-chloro-sorbic acid, angelic acid, cinnamic acid, 4-chloro-cinnamic acid, β-styryl-acrylic acid (1-carboxy-4-phenyl-1,3-butadiene), itaconic acid, citraconic acid, mesaconic acid, glutaconic acid, aconitic acid, maleic acid, fumaric acid, tricarboxyethylene and maleic acid anhydride and salts (e.g., alkali metal salts such as sodium, potassium and lithium salts) thereof. For forming any polymer to be present at the lesion-contacting surface of the composition, the monomer or monomer mixture will include a monomer containing pendant sulphonyl groups, e.g., —SO$_3$ in acid or salt form.

Olefinically unsaturated sulphonic acid monomers include aliphatic or aromatic vinyl sulphonic acids such as vinylsulphonic acid, allylsulphonic acid, vinyltoluenesulphonic acid and styrene sulphonic acid; vinyl sulphobetaines such as SPDA (1-propanaminium N,N-dimethyl-N-[2-[(1-oxo-2-propenyl)oxy]-3-sulfo hydroxide, inner salt (available from Raschig); acrylic and methacrylic sulphonic acid such as sulphoethyl acrylate, sulphoethyl methacrylate, sulphopropyl acrylate, sulphopropyl methacrylate, 2-hydroxy-3-acryloxy propyl sulphonic acid, 2-hydroxy-3-methacryloxy propyl sulphonic acid and 2-acrylamido-2-methyl-propanesulphonic acid and salts (e.g., ammonium or alkali metal salts, such as sodium, potassium and lithium salts, or alkaline earth metal salts, such as calcium or magnesium) thereof.

The monomers may suitably be used in admixture with each other or with other monomers. In one particularly useful embodiment of the invention, a monomer which has a first counter-cation associated with it may be used in admixture with one or more monomer which has/have one or more second/further counter-cation(s) associated with it/them. The first counter-cation and the second/further counter cation may be the same or different. The monomers in their anionic form (i.e., disregarding the counter-cation) may be the same or different. In this way, the proportions of different cations (e.g., alkali metal ions such as sodium or potassium, or ammonium ions) can be finely controlled in the resultant polymer (homopolymer or copolymer). The particular weight ratios of one monomer to the or each other monomer can be selected within wide limits by those skilled in the art, depending on the desired properties of the resultant hydrogel polymer.

Further examples of suitable monomers for use in the present invention include: a polyalkylene glycol acrylate or a substituted derivative thereof; a polyalkylene glycol methacrylate or a substituted derivative thereof; acrylic acid and salts thereof (e.g., alkali metal salts such as sodium, potassium and lithium salts); 2-acrylamido-2-methyl-propanesulphonic acid and salts thereof (e.g., ammonium or alkali metal salts, such as sodium, potassium and lithium salts, or alkaline earth metal salts, such as calcium or magnesium); acrylic acid (3-sulphopropyl) ester or a substituted derivative thereof or a salt thereof (e.g., an alkali metal salt such as sodium, potassium or lithium salt); diacetone acrylamide (N-1,1-dimethyl-3-oxobutyl-acrylamide); a vinyl lactam (e.g., N-vinyl pyrrolidone or a substituted derivative thereof); an optionally substituted N-alkylated acrylamide such as hydroxyethyl acrylamide; and an optionally substituted N,N-dialkylated acrylamide; and/or N-acryloyl morpholine or a substituted derivative thereof. For forming any polymer of the hydrogel, which may in use contact the wound, the monomer or monomer mixture may include a monomer containing pendant sulphonyl groups, e.g., —$SO_3^-$ in acid or salt form, and optionally carboxylic groups in acid or salt form.

Particularly preferred monomers include: the sodium salt of 2-acrylamido-2-methylpropane sulphonic acid, commonly known as NaAMPS, which is available commercially at present from Lubrizol as either a 50% aqueous solution (reference code LZ2405) or a 58% aqueous solution (reference code LZ2405A); acrylic acid (3-sulphopropyl) ester potassium salt, commonly known as SPA or SPAK (SPA or SPAK is available commercially in the form of a pure solid from Raschig); acrylic acid (3-sulphopropyl) ester sodium salt, commonly known as SPANa (SPANa is available in the form of a pure solid from Raschig); N-acryloyl morpholine; and hydroxyethyl acrylamide.

The above monomers and monomer types may optionally include substituent groups. Optional substituents of the monomers used to prepare the hydrogels used in the present invention may preferably be selected from substituents which are known in the art or are reasonably expected to provide polymerisable monomers which form hydrogel polymers having the properties necessary for the present invention. Suitable substituents include, for example, lower alkyl (e.g., $C_1$ to $C_{10}$, optionally $C_1$ to $C_5$), hydroxy, halo and amino groups.

Cross-Linking Agents

Conventional cross-linking agents are suitably used to provide the necessary mechanical stability and to control the adhesive properties of the hydrogel. The amount of cross-linking agent required will be readily apparent to those skilled in the art such as from about 0.01% to about 0.5%, particularly from about 0.05% to about 0.4%, most particularly from about 0.08% to about 0.3%, by weight of the total polymerisation reaction mixture. Typical cross-linkers include tripropylene glycol diacrylate, ethylene glycol dimethacrylate, triacrylate, polyethylene glycol diacrylate (polyethylene glycol (PEG) molecular weight between about 100 and about 4000, for example PEG400 or PEG600), and methylene bis acrylamide.

Organic Plasticisers

The hydrogel and/or its pre-gel may comprise one or more organic plasticisers. The one or more organic plasticisers may suitably comprise any of the following either alone or in combination: at least one polyhydric alcohol (such as glycerol, polyethylene glycol, or sorbitol), at least one ester derived therefrom, at least one polymeric alcohol (such as polyethylene oxide) and/or at least one mono- or poly-alkylated derivative of a polyhydric or polymeric alcohol (such as alkylated polyethylene glycol). Glycerol is the preferred plasticiser. An alternative preferred plasticiser is the ester derived from boric acid and glycerol. When present, the organic plasticiser may comprise up to about 45% by weight of the hydrogel composition.

Surfactants

Any compatible surfactant may optionally be used as an additional ingredient of the hydrogel composition. Surfactants can lower the surface tension of the mixture before polymerisation and thus aid processing. The surfactant or surfactants may be non-ionic, anionic, zwitterionic or cationic, alone or in any mixture or combination. The surfactant may itself be reactive, i.e., capable of participating in the hydrogel-forming reaction. The total amount of surfactant, if present, is suitably up to about 10% by weight of the hydrogel composition, preferably from about 0.05% to about 4% by weight.

In a preferred embodiment of the invention the surfactant comprises at least one propylene oxide/ethylene oxide block copolymer, for example such as that supplied by BASF Plc under the trade name Pluronic P65 or L64.

Other Additives

The hydrogel in the composite of the present invention may include one or more additional ingredients, which may be added to the pre-polymerisation mixture or the polymerised product, at the choice of the skilled worker. Such additional ingredients are selected from additives known in the art, including, for example, water, organic plasticisers, surfactants, polymeric material (hydrophobic or hydrophilic in nature, including proteins, enzymes, naturally occurring polymers and gums), synthetic polymers with and without—pendant carboxylic acids, electrolytes, pH regulators, colourants, chloride sources, bioactive compounds and mixtures thereof. The polymers can be natural polymers (e.g., xanthan gum), synthetic polymers (e.g., polyoxypropylene-polyoxyethylene block copolymer or poly-(methyl vinyl ether alt maleic anhydride)), or any combination thereof. By "bioactive compounds" we mean any compound or mixture included within the hydrogel for some effect it has on living systems, whether the living system be bacteria or other microorganisms or higher animals such as the patient. Bioactive compounds that may be mentioned include, for example, pharmaceutically active compounds, antimicrobial agents, antiseptic agents, antibiotics and any combination thereof. Antimicrobial agents may, for example, include: sources of oxygen and/or iodine (e.g., hydrogen peroxide or a source thereof and/or an iodide salt such as potassium iodide) (see, for example Bioxzyme technology, for example in The Sunday Telegraph (UK) 26 Jan. 2003 or the discussion of the Oxyzyme system at www.wounds-uk.com/posterabstracts2003.pdf); honey (e.g., active Manuka honey); antimicrobial metals, metal ions and salts, such as, for example, silver-containing antimicrobial agents (e.g., colloidal silver, silver oxide, silver nitrate, silver thiosulphate, silver sulphadiazine, or any combination thereof); or any combination thereof.

In the Bioxzyme system, a dressing comprises two hydrogels. One contains glucose based antibacterial compounds and the other contains enzymes that convert the glucose into hydrogen peroxide. When these are exposed to air and contacted together at a wound site, the enzyme-containing gel being adjacent the skin and the glucose-containing gel overlying the enzyme-containing gel, a low level steady flow of hydrogen peroxide is produced, which inhibits anaerobic bacteria. This antibacterial effect can be enhanced by the inclusion of a very low level of iodide (less than about 0.04%) in the hydrogel. The hydrogen peroxide and the iodide react to produce iodine, a potent antimicrobial agent.

Hydrogels incorporating antimicrobial agents may, for example, be active against such organisms as *Staphylococcus aureus* and *Pseudomonas aeruginosa*.

Additional polymer(s), typically rheology modifying polymer(s), may be incorporated into the polymerisation reaction mixture at levels typically up to about 10% by weight of total polymerisation reaction mixture, e.g., from about 0.2% to about 10% by weight. Such polymer(s) may include polyacrylamide, poly-NaAMPS, polyethylene glycol (PEG), polyvinylpyrrolidone (PVP) or carboxymethyl cellulose.

The hydrogel preferably used in the present invention may consists essentially of a cross-linked hydrophilic polymer of a hydrophilic monomer and optionally one or more comonomer, together with water and/or one or more organic plasticiser, and optionally together with one or more additives selected from surfactants, polymers, pH regulators, electrolytes, chloride sources, bioactive compounds and mixtures thereof, with less than about 30%, optionally less than about 20%, optionally less than 10% by weight of other additives.

The water activity, which is related to the osmolarity and the ionic strength of the precursor solution (as measured, for example, by a chilled mirror dewpoint meter, Aqualab T3) is preferably between 0.05 and 0.99, more preferably between, 0.2 and 0.99, even more preferably between 0.3 and 0.98 and even more preferably between 0.4 and 0.8. The higher the ionic strength, reflected in a lower water activity, the lesser the swelling of the fibre structure. The ionic strength of the precursor solution can therefore be used to optimise the hydrogel composite properties.

For further details of the hydrogel material for use in the present invention, and its preparation, please refer to the following publications: PCT Patent Applications Nos. WO-97/24149, WO-97/34947, WO-00/06214, WO-00/06215, WO-00/07638, WO-00/46319, WO-00/65143, WO-01/96422 and WO 2007/007155, the disclosures of which are incorporated herein by reference.

Optional Components

One or more porous sheets, for example a scrim, may be disposed within or on a surface of one or more of the layers, preferably the first layer, and preferably within or on a surface of the gel material, preferably a hydrogel material. A scrim includes, but is not limited to, porous sheets comprising materials selected from woven, non-woven and net materials. Such a scrim material may be formed of a material that is natural in origin, synthetic in origin, or partly natural and partly synthetic. The scrim may suitably be in the form of a net or a woven or non-woven fabric. Preferred scrims include those formed from polyolefins, polyamides, polyacrylates, or polyesters, for example non-wovens, foams or nets. Suitable non-woven scrims are available from HDK Industries Inc. (USA). The scrim material may, for example, comprise sodium polyacrylate fibres, such as those commercially available under the tradename Oasis™ from Acordis Technical Absorbents Limited. The scrim is preferably provided by introducing it into a laid down (e.g., cast) layer of a pre-gel liquid precursor for the hydrogel material, before curing, so that the liquid pre-gel covers and surrounds the scrim. On curing of the liquid pre-gel, the hydrogel is thereby formed encapsulating the scrim material. Use of a scrim material in this way is found to be potentially helpful in enhancing the strength and ease of handling of the hydrogel component and/or the finished dressing.

The material comprising the second layer is, but not limited to, preferably a moisture vapour permeable non woven fibre and includes but not limited to those formed from a material that is natural in origin, synthetic in origin, or partly natural and partly synthetic including but not limited to cellulose, cotton, polyolefins, polyamides, polyacrylates, or polyesters. Suitable non-woven materials are available from Fibreweb Tecnofibra S.p.A. (Italy), for example Tecnojet B-650. The non-woven density has a density greater than 50 and less than 500 g/ml.

The third layer preferably comprises a material with a tensile strength greater than 15 N/25 mm, more preferably greater than 25 N/25 mm and even more preferably greater than 35 N/25 mm. It additionally comprises a percentage elongation to break greater than 100, more preferably greater than 200 and even more preferably greater than 400. The material also comprises a medical grade adhesive coated on one side with a coat weight greater than 10 g/m$^2$, more preferably greater than 20 g/m$^2$ and even more preferably greater than 30 g/m$^2$ but preferably less than 100 g/m$^2$. Preferably the material comprises a polyurethane and more preferably comprises a polyurethane film/foam composite, Suitable materials for the third layer are available from Exopack (UK). A suitable example is Inspire 7235.

The fourth layer preferably comprises a flexible film which can be formed from a material natural or synthetic in origin and includes but not limited to polyolefins, polyurethanes, polyamides, polyacrylates, or polyesters. The material preferably has a tensile strength greater than 10 N/25 mm and more preferably greater than 15 N/25 mm. The elongation to break is preferably greater than 100% more preferably greater than 250%. Suitable materials are available from Exopack UK, for example Inspire 2301, a cast polyurethane film.

Where an optional fifth layer is used, as described above, this optional fifth layer preferably comprises a double sided adhesive coated film. The adhesive is preferably a hypoallergenic pressure sensitive adhesive with a peel strength adhesion to stainless steel preferably greater than 3 N/25 mm, more preferably greater than 5 N/25 mm but less than 25 N/25 mm. Suitable materials are available from 3M (US). A suitable example is 3M Double Coated Medical tape Product Number 1522.

The construction of the dressing of the present invention is designed to allow excellent adherence to the body when applied in a wide variety of environmental conditions. These include, desert, tropical rain forest and arctic conditions. The dressing will also remain adherent in the presence of body fluids including blood. The flutter valve will close (i.e., form a seal) with a slight negative pressure. Typically the pressure in the intrapleural cavity is 4 mm Hg (or approximately 5 cm H$_2$O) less than the pressure in the alveoli of the lungs (which always equalizes with the atmospheric pressure outside of the body). It is this negative relative pressure in the intrapleural cavity that keeps the lungs from collapsing during expiration. On inspiration the intrapleural pressure decreases by about 3 cm H$_2$O to 5 cm. H$_2$O To form a seal on a penetrating chest wound on inspiration the flutter valve must therefore become operational with a negative pressure not greater than 5 cm H$_2$O, preferably less. This will also be reflected in the rate of decrease in pressure. It has been found that prior art dressings tested in vitro (a rectangular metal box with an internal volume of circa 3.8 liters with a centrally placed hole (circa 4.5 cm$^2$) over which the dressings are mounted) require a much higher and sustained air removal flow to achieve a 5 cm H$_2$O pressure reduction as measured by a water manometer connected to the 10 mm external diameter tube used to evacuate the air in the box. The flutter valve construction also requires minimal negative pressure to seal in the presence of fluid.

Use of Certain Hydrogels in Chest Seal Dressings

The use of certain ones of the above specifically identified hydrogels in dressings for use in dressing penetrating chest wounds is itself new and therefore constitutes a further aspect of the present invention.

This further aspect is itself inventive whatever the number and construction of the one-way valve(s), because the use of these particular hydrogel skin adhesives had not at all been considered for use in this area of trauma treatment, despite long existence and recognition in the hospital and clinical environment. The present inventors have realised for the first time that certain highly engineered hydrogels in fact are robust enough and suitable for field conditions such as chest trauma, and can play an extremely valuable role in saving lives under those conditions.

Therefore, in a further aspect the present invention provides a dressing for covering a wound of a patient suffering from a penetrating chest wound, comprising a sheet member adapted to be adhered to the patient's skin in use to provide an airtight seal around a space defined by the dressing over the wound, and at least one valve permitting one-way air, blood and/or other fluid flow communication from the space above the wound to the exterior of the dressing, wherein the sheet member is adapted to be adhered to the patient's skin in use by being provided with a skin-adhesive coating comprising a hydrated polymer formed by polymerisation of one or more monomer selected from olefinically unsaturated aliphatic or aromatic vinyl sulphonic acids, vinyl sulphobetaines, acrylic and methacrylic sulphonic acid esters, 2-hydroxy-3-acryloxy propyl sulphonic acid, 2-hydroxy-3-methacryloxy propyl sulphonic acid, 2-acrylamido-2-methyl-propanesulphonic acid and salts thereof.

The dressing according to this further aspect may be used in conjunction with any one or combination of the features, examples and embodiments described herein in relation to other aspects of the invention.

General Applicability of Described Features Etc.

Where, in the discussion herein, a feature or example or preference has been described in relation to one aspect of the invention, it will be understood that it is equally applicable to describing the corresponding feature or example or preference in relation to each of the other aspects of the invention.

BRIEF DESCRIPTION OF THE DRAWINGS

The invention will now be described further, without limitation and purely by way of example, with reference to the accompanying drawings, in which.

DETAILED DESCRIPTION OF THE DRAWINGS

Figure 1:
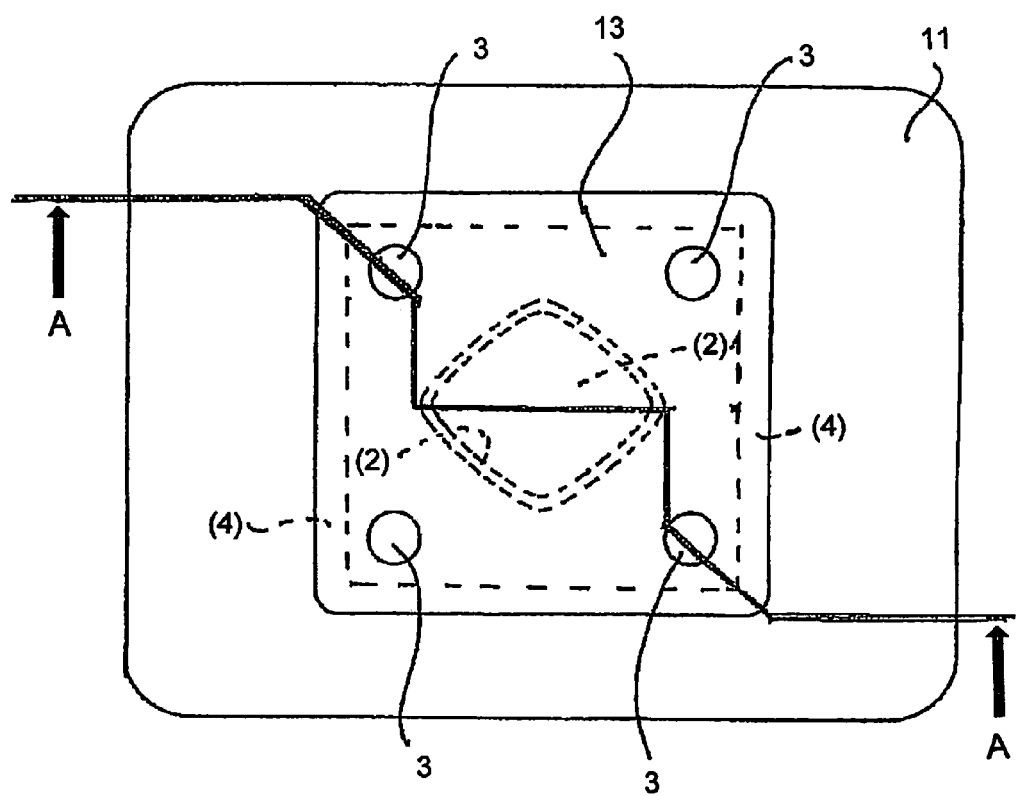
FIG. 1 shows a top view of a wound dressing.

In FIG. 1, features that are invisible from above (unless the layers or some of them are transparent or translucent) are depicted in dotted lines. For clarity, however, the tags 16 and 17 of the release sheet 15 are not shown in FIG. 1.

Figure 2:
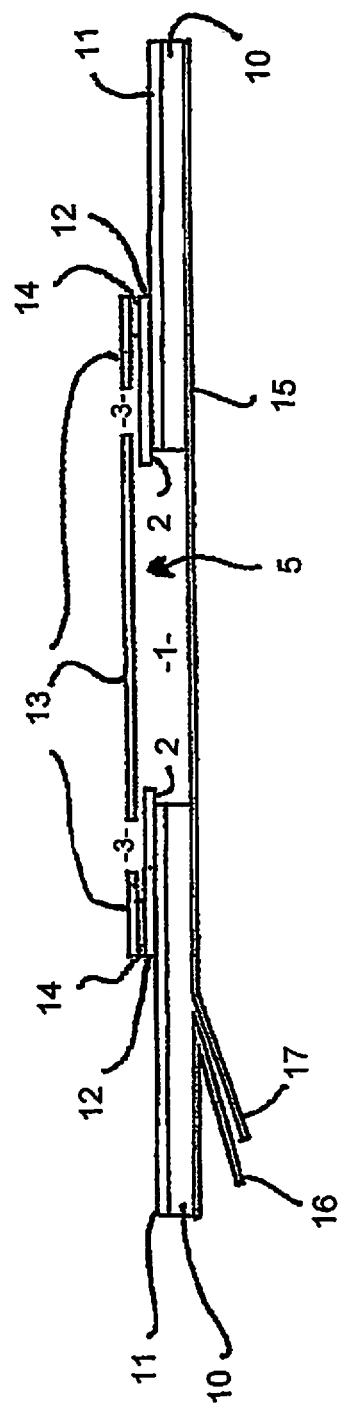
FIG. 2 shows a schematic cross-section along the line A-A of FIG. 1, looking in the direction of the arrows.

Referring to FIGS. 1 and 2, there is shown generally an embodiment of a multilayered wound dressing structure comprising five main layers 10, 11, 12, 13 and 14.

Layer 10 comprises a water absorbent gel, preferably a hydrogel, that in use contacts the skin area surrounding the wound. It optionally comprises one or more porous scrims.

Layer 11 comprises a backing material, for example a breathable non-woven material.

Layer 12 comprises a foam/film composite material with an acrylic adhesive coated on to the wound-facing face.

Layer 13 is a flexible film acting as an upper movable layer serving a plurality of flutter valves, as will be described in greater detail below.

Layer 14, which may be omitted or replaced by alternative means of securement between layers 11 and 13, is a film coated on both sides with an adhesive.

In this embodiment a conventional release sheet (e.g., of siliconised paper or non-stick plastic) constitutes a bottom layer 15, not counted in the five mentioned above. This release sheet is split into two parts in conventional manner, to provide a pair of pull tags 16, 17 by which the release sheet can be grasped for peeling off.

Overlain over the upper surface of the bottom layer 15, and provided with a central aperture 1 where the wound will be in use, is the first layer of the dressing, constituted by a skin-adhesive layer 10.

Overlain over the total upper surface of the skin-adhesive layer 10, and also provided with a corresponding aperture 1 where the wound will be in use, is the second layer, constituting a backing material layer 11 for the dressing. This layer 11 provides mechanical support to the skin-adhesive layer and prevents the upper surface of the skin-adhesive layer 10 from sticking to external objects in use. The backing material is suitably chosen for strength and lightness, as well as flexibility and skin-conformability, and to provide a pleasant touch sensation when touching the external surface of the dressing directed away from the skin.

Overlain over a region (in this embodiment not the total area 0 of the upper surface of the backing material layer 11 is a third layer 12 which provides an anchor for sealing the fourth layer 13 (described below) that forms the moveable parts of the flutter valves. The third layer 12 of the dressing is provided with an aperture generally corresponding to the aperture 1 of the first and second layers where the wound will be in use. However, the aperture in the third layer is smaller than the aperture 1 in the first and second layers described previously, so that a flange 2 of the material of the third layer extends into the aperture 1 of the first 10 and second 11 layers around its periphery, by a distance of about 0.2 to about 1 cm, preferably about 0.5 cm. By selecting the material of the third layer 12 to be of suitable flexibility, and providing a suitable skin-adhesive coating on the underside of the flange 2, the flange can in use stick to the skin surrounding the wound and thereby enhance the air-tight seal around the wound as well as restricting direct contact between blood and other wound fluids and the skin-adhesive of the first layer 10.

The skin-adhesive of the flange 2 provided by the third layer, as described above, is protected before use by the release layer 15 mentioned above.

The fourth layer 13 overlies the upper surface of the third layer 12, and is formed of a thin film having sufficient flexibility to serve as the moveable portions of the plurality of flutter valves. This layer has no aperture corresponding to the apertures of the first to third layers mentioned above, but instead a plurality of holes 3 near its periphery, these holes being dimensioned and arranged to serve in use as the mouths of the flutter valves. The fourth layer 13 is non-adhesive on both major faces, and is sealed to the upper surface to the third layer 13 in a seal line 4 around its periphery, ensuring that the holes 3 are free to open and close in use in flutter valve manner, cooperating with the underlying portion of the upper surface of the third layer 11.

The seal line 4 in the illustrated embodiment is provided by the fifth layer 14, which is composed of a strip of double-sided adhesive film arranged under the border of the fourth layer 13.

The holes 3 of the fourth layer as illustrated are circular, but may be shaped in any convenient way to have minimal sharp corners of other points where the material of the fourth layer 13 can become stressed during working of the flutter valves.

The layers are suitably secured together by appropriate conventional means, for example gluing, melt-welding, heat welding, ultrasound welding, or any combination thereof. Of course, where a layer has its own adhesiveness, it may be adhered directly to an adjacent layer.

As illustrated in FIG. 2, a gap is shown between layers 11 and 13. However, this is simply to show more clearly the arrangement of the fifth layer 14 which provides the seal line 4 around the periphery of the fourth layer 13. In practice, the layer 13 will be quite tight and the parts of it that lie between a hole 3 and the central region of the dressing will lie flat and in contact with the upper surface of the third layer 12. Only when there is an overpressure of air, or liquid, in the space 5 defined above the wound in use will the fourth layer 13 move apart from the upper surface of the third layer 12. However, when there is no overpressure, or an underpressure in the space 5 defined above the wound, the fourth layer 13 will be pressed against the upper surface of the third layer 12 by the tautness of the fourth layer 13 and/or by external atmospheric pressure, so providing the flutter valve action according to the present invention.

Figure 3:
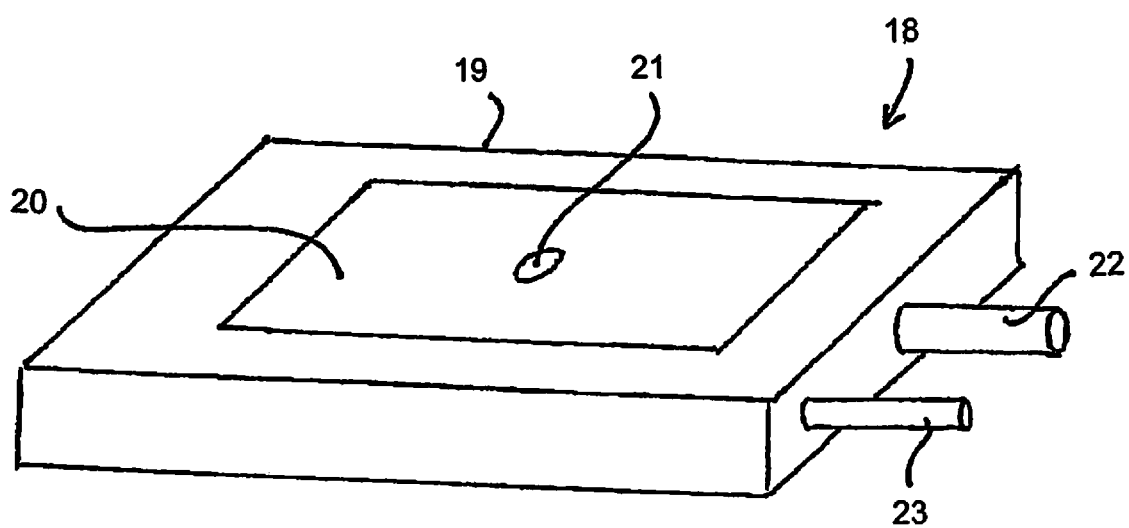
FIG. 3 shows a schematic view of a test chamber for testing the performance of the wound dressing of FIGS. 1 and 2.

Referring now to FIG. 3, there is shown a schematic view of a test chamber 18 used for evaluating the chest seal performance of wound dressings, including but not limited to the dressing illustrated in FIGS. 1 and 2.

The test chamber 18 comprises a stainless steel box 19, for example of dimensions 270 mm×270 mm×60 mm (providing a 4.2 liter internal volume), with a rectangular opening in the top of the box onto which is placed a stainless steel plate 20 which is removably held in position by adjustable clamps, not shown, which clamp the plate 20 to a rubber seal (not shown) which extends airtightly between the plate 20 and the top portion of the box 19. For use with the stated 4.2 liter box the plate suitably has dimensions 260 mm×200 mm×2 mm and the rectangular opening of the top of the box 19 is only slightly larger than 260 mm×200 mm. The plate 20 which has a circular orifice 21, suitably about 28 mm in diameter, centrally located. In this way, the size of the orifice 21 can be adjusted as desired, by using a range of plates 20. An air inlet/outlet port 22 leading to a suitable pump (not shown), for example a bellows pump, and a pressure gauge port 23 leading to a conventional pressure gauge having a typical range of −40 cm H$_2$O to +40 cm H$_2$O) (pressure gauge not shown) are located on one side of the chamber 18 and air-flow communicate between the interior of the box 19 and the respective pump or gauge.

Figure 4:
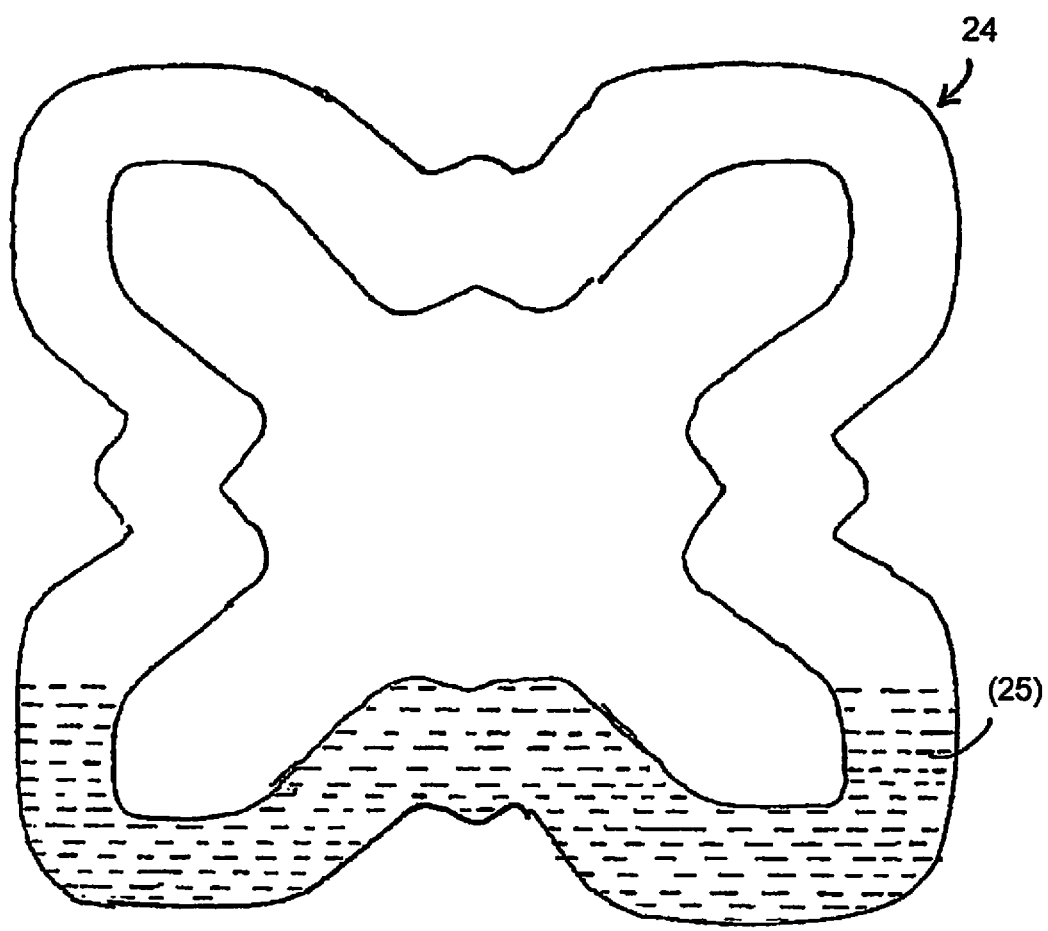
FIG. 4 shows a top view of a spacer device suitable for use with the wound dressing of FIGS. 1 and 3.

Referring finally to FIG. 4, there is shown a top view of a spacer device 24 suitable for use with wound dressings, including but not limited to the dressing illustrated in FIGS. 1 and 2.

The illustrated spacer device 24 is constructed as a complete ring of rigid internally corrugated sheet material, for example an internally corrugated plastic sheet, having continuous major faces spaced apart by the internal corrugations with a face-to-face thickness about 0.25 cm. An adhesive is provided on the lower major face (not shown) so that the spacer 24 can be stuck to the face of the dressing that is directed away from the patient's skin in use. The internal corrugations are shown by dotted lines 25 in FIG. 4 (although the corrugations are shown for only a portion of the device 24, they will correspondingly be present over the whole device).

The spacer device 24 is illustrated at approximately full size for use with a typical adult human chest seal dressing according to FIGS. 1 and 2, so that the ring will encircle all the flutter valves 3 of the dressing. The ring has a shape corresponding generally to the shape of the dressing, but a little smaller than the outside limits of the dressing. The internal corrugations 25 of the spacer device 24 provide through-holes between the radially inward and radially outward sides of the ring, which allow air, blood and other fluid to pass from the encircled region above the flutter valves 3 to the external atmosphere when the spacer is in place on the dressing, when an external object such as clothing, a blanket or a thermal insulating sheet is laid over the dressing and spacer.

EXAMPLES

The present invention will now be further illustrated with reference to the following non-limiting Examples.

Example 1

This Example shows particular materials and a method by which the embodiment of the dressing illustrated in FIGS. 1 and 2 may be constructed.

First Part
First Layer 10
A 200 mm by 150 mm sample cut from an adhesive hydrogel with an integral non-woven scrim made in accordance with the above description, designated as FW 206, available from First Water Ltd, UK).

Second Layer 11
A 200 m by 150 mm sample cut from a non-woven material (Tecnojet B-650, Fibreweb Tecnofibra S.p.A. (Italy)).

Layer 11 was laminated to layer 10 and then a centrally located 40 mm by 40 mm diamond shaped aperture 1 was cut through both layers.

Second Part
Third Layer 12
A centrally located 35 mm by 35 mm diamond shaped aperture was cut into a 110 mm by 100 mm polyurethane film/foam composite (Inspire 7235, Exopack, UK).

Fourth Layer 13
Four circular 12.5 mm diameter apertures were cut into a cast polyurethane film, Inspire 2301, Exopack UK. The apertures were located with the centres 25 mm from the outer edge of the layer along the line between diagonally opposed corners.

Fifth Layer 14
A centrally located 90 mm by 80 mm aperture was cut into 110 mm by 100 mm double sided adhesive polyethylene film, Double Coated Medical tape Product Number 1522 (3M, US).

The dressing was assembled by placing layer 12 onto the laminate formed in the First Part, such that the perimeter of the apertured area of layer 12 overlapped into the aperture 1 through the laminate. Then layer 14 was placed onto layer 12 such that layer 14 surrounds the aperture in layer 12. Finally, layer 13 was placed onto layer 14 such that the apertures in layer 13 were within the aperture in layer 14. A small amount of pressure was applied to assist in the lamination of the layers.

The finished assembly was mounted on a release sheet 15 and packaged for storage and transportation.

The final assembled dressing was able to allow the flow of air and fluid in the direction of layer 10 to layer 13 but prevented the reverse flow.

Example 2

This Example describes the testing process and test data relating to the dressing of the present invention.

Test Method

To test the performance of the chest seal dressing illustrated in FIGS. 1 and 2 and constructed as described in Example 1, and to compare it against dressings of the prior art, the test chamber 18 as illustrated in FIG. 3 was used.

A dressing to be tested is placed on the removable plate, held in place by the adhesive present on the dressing, with the one way valve assembly of the dressing centrally positioned over the orifice 21 in the removable plate 23.

A known volume of air in excess of the volume of atmospheric air starting in the test chamber 18 (for example, selected from a range of 50 cc to 500 cc) is then pumped in and out of the chamber 18 by means of the pump, at a known rate (for example, selected from a range of 2 to 40 cycles (in and out is one cycle) per minute. The pressure inside the chamber 18 is constantly monitored by the pressure gauge, which suitably has a measurement range encompassing −40 to +40 cm $H_2O$. If the valve system of the dressing closes effectively on removal of air from the chamber then the pressure inside the chamber will decrease. Measured values of decrease at less than about −20 cm $H_2O$ are indicative of the formation of a good seal.

When air is pumped into the chamber the pressure will increase until such time as the one way valve system of the dressing opens. It is this valve opening pressure that is of critical importance in the performance of a chest seal dressing. If the valve opening pressure is too high, it is possible that during the breathing cycles of a patient with a penetrating chest wound the valve will not open and consequently this would increase the risk of a tension pneumothorax.

In the tests below a test chamber was used in which the dimensions of the box 19 were 270 mm×270 mm×60 mm (providing a 4.2 liter internal volume), the dimensions of the plate 20 were 260 mm×200 mm×2 mm, and the diameter of the orifice 21 was 28 mm in diameter. The excess air in/out volume was 400 cc and the pump rate for this was 30 cycles per minute.

Sample dressings (a) as described above in Example 1 according to the present invention, (b) the marketed Hyfin Vent Chest Seal (North American Rescue LLC, Greer, S.C., USA; http://www.narescue.com/HyFin_Vent_Chest_Seal-CNB3327DB2521D.html?BC=3C7457EA9AFA), (c) the marketed Bolin Chest Seal, and (d) the marketed Asherman Chest Seal were tested using the test system described in the preceding paragraph for a two hour period. The test results are shown below.

Test Results

All the dressings tested produced a pressure in the chamber on evacuation of air over the test period of on average less than −30 cm $H_2O$, indicative of the formation of a good seal. However the average valve opening pressures were different as shown in the table below.

| Dressing | Average Opening Pressure (cm $H_2O$) | Standard deviation |
|---|---|---|
| (a) Present Invention | +0.4 | 0.2 |
| (b) Hyfin Vent Chest Seal | +8.8 | 1.2 |
| (c) Bolin Chest Seal | +9.9 | 2.4 |
| (d) Asherman Chest Seal | +2.6 | 0.2 |

The data show that the dressing of the present invention has significantly lower opening pressure than commercially available prior art.

The foregoing broadly describes the present invention without limitation to particular embodiments. Variations and modifications as will be within the abilities of those skilled in this art are intended to be included in the scope of this invention as defined in and by the appended claims.

What is claimed is:

1. A dressing for covering a wound of a patient, comprising:
   a sheet member adapted to be adhered to the patient's skin in use to provide an airtight seal around the wound, wherein the sheet member is adapted to be spaced apart from the skin in the region of the wound to define in use a space above the wound, and
   a plurality of mutually spaced-apart flutter valves permitting one-way air, blood and/or other fluid flow communication from the space above the wound to the exterior of the dressing,
   wherein the sheet member is a multilayer sheet member comprising a first layer nearest the patient's skin in use and at least one additional layer overlying at least a portion of the first layer on the major face thereof directed away from the patient's skin in use, and
   wherein the first layer is skin-adhesive on the major face that is directed towards the patient's skin in use, and an aperture is provided in the first layer, so that the first layer can surround the wound, but not adhere to it, when the first layer is positioned on the patient's skin to surround the wound and adheres to the patient's skin around the wound to provide an airtight seal to the skin around the wound.

2. The dressing according to claim 1, wherein the dressing, including the flutter valves, is formed from one or more sheet materials which are of sufficient flexibility that the whole dressing is skin-conformable and the sheet material has substantially no rigid parts.

3. The dressing according to claim 1, wherein the at least one additional layer comprises a film layer which overlies the wound encircling aperture above the major face of the first layer of the sheet member that is directed away from the skin in use, and extends radially outwardly to overlie a portion of the first layer of the sheet member around the aperture,
   wherein the film layer is sealed to the first layer of the sheet member and is provided with a plurality of holes defining the mouths of the plurality of flutter valves of the dressing, and
   wherein the flutter valves permit one-way air, blood and/or other fluid flow communication from the space above the wound to the exterior of the dressing.

4. The dressing according to claim 1, wherein the dressing has two or three flutter valves.

5. The dressing according to claim 1, wherein the dressing has four flutter valves.

6. The dressing according to claim 1, wherein the dressing has five flutter valves.

7. The dressing according to claim 1, wherein the sheet member includes skin-adhesive coating comprising one or more gels, hydrocolloids, pressure-sensitive adhesives or any combination thereof.

8. The dressing according to claim 7, wherein the skin-adhesive coating comprises a hydrogel.

9. The dressing according to claim 8, wherein the hydrogel comprises a hydrated polymer formed by polymerisation of one or more monomers selected from olefinically unsaturated aliphatic or aromatic vinyl sulphonic acids, vinyl sulphobetaines, acrylic and methacrylic sulphonic acid esters, 2-hydroxy-3-acryloxy propyl sulphonic acid, 2-hydroxy-3-methacryloxy propyl sulphonic acid and 2-acrylamido-2-methyl-propanesulphonic acid and salts thereof.

10. A dressing for covering a wound of a patient, comprising:
   a sheet member adapted to be adhered to the patient's skin in use to provide an airtight seal around the wound, wherein the sheet member is adapted to be spaced apart from the skin in the region of the wound to define in use a space above the wound,
   a plurality of mutually spaced-apart flutter valves permitting one-way air, blood and/or other fluid flow communication from the space above the wound to the exterior of the dressing, and
   a spacer device which comprises:
      one or more outwardly extending projections which in use extend in the region of the flutter valves of the dressing and serve to space external objects away from the dressing to prevent the flutter valves from being pressed closed by the external objects, and
      apertures being present through the projection(s) and/or between projections so that air, blood and other fluid can pass from a space above the flutter valves to the external atmosphere when the spacer is in place on the dressing, when an external object is laid over the dressing and spacer.

11. A dressing for covering a wound of a patient, comprising:
   a sheet member adapted to be adhered to the patient's skin in use to provide an airtight seal around the wound,
   one or more mutually spaced-apart flutter valves permitting one-way air, blood and/or other fluid flow communication from a space above the wound to the exterior of the dressing,
   wherein the dressing has a threshold valve-opening over-pressure of less than about 2.2 cm $H_2O$, and
   a spacer device which comprises:
      one or more outwardly extending projections which in use extend in the region of the flutter valves of the dressing and serve to space external objects away from the dressing to prevent the flutter valves from being pressed closed by the external objects, and
      apertures being present through the projection(s) and/or between projections so that air, blood and other fluid can pass from a space above the flutter valves to the external atmosphere when the spacer is in place on the dressing, when an external object is laid over the dressing and spacer.

12. The dressing according to claim 11, wherein the dressing has two, three, four or five valves.

13. The dressing according to claim 11, wherein the sheet member includes skin-adhesive coating comprising a hydrated polymer formed by polymerisation of one or more monomer selected from olefinically unsaturated aliphatic or aromatic vinyl sulphonic acids, vinyl sulphobetaines, acrylic and methacrylic sulphonic acid esters, 2-hydroxy-3-acryloxy propyl sulphonic acid, 2-hydroxy-3-methacryloxy propyl sulphonic acid, 2-acrylamido-2-methyl-propanesulphonic acid and salts thereof.

14. A dressing for covering a wound of a patient suffering from a penetrating chest wound, comprising:
   a sheet member adapted to be adhered to the patient's skin in use to provide an airtight seal around a space defined by the dressing over the wound,
   at least one mutually spaced-apart flutter valve permitting one-way air, blood and/or other fluid flow communication from the space above the wound to the exterior of the dressing,
   wherein the sheet member is adapted to be adhered to the patient's skin in use by being provided with a skin-adhesive coating comprising a hydrated polymer formed by polymerisation of one or more monomer selected from olefinically unsaturated aliphatic or aromatic vinyl sulphonic acids, vinyl sulphobetaines, acrylic and methacrylic sulphonic acid esters, 2-hydroxy-3-acryloxy propyl sulphonic acid, 2-hydroxy-3-methacryloxy propyl sulphonic acid, 2-acrylamido-2-methyl-propanesulphonic acid and salts thereof, and
   a spacer device which comprises:
      one or more outwardly extending projections which in use extend in the region of the flutter valves of the dressing and serve to space external objects away from the dressing to prevent the flutter valves from being pressed closed by the external objects, and
      apertures being present through the projection(s) and/or between projections so that air, blood and other fluid can pass from a space above the flutter valves to the external atmosphere when the spacer is in place on the dressing, when an external object is laid over the dressing and spacer.

15. The dressing according to claim 14, wherein the dressing has two, three, four or five valves.

* * * * *